(12) United States Patent
Chiapperi et al.

(10) Patent No.: US 6,310,337 B1
(45) Date of Patent: *Oct. 30, 2001

(54) METHOD OF PRESELECTING FLASHLAMP VOLTAGES FOR ASSAYS

(76) Inventors: Joseph M. Chiapperi, 150 Winesap Pt., Rochester, NY (US) 14612; Donald M. Josephson, 8 Province Dr., Rochester, NY (US) 14624; Stuart G. MacDonald, 4663 E. Lake Rd., Pultneyville, NY (US) 14538

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/366,247

(22) Filed: Aug. 3, 1999

Related U.S. Application Data
(60) Provisional application No. 60/096,361, filed on May 13, 1998.

(51) Int. Cl.[7] ............................................. G01J 1/32
(52) U.S. Cl. ..................................... 250/205; 250/559.4
(58) Field of Search ................................ 250/205, 559.4, 250/461.2, 214 R, 483.1, 484.2, 487.1; 356/39–41, 73; 436/530, 519

(56) References Cited
U.S. PATENT DOCUMENTS

| | | | |
|---|---|---|---|
| 4,003,662 | 1/1977 | Erich et al. | 356/206 |
| 4,117,375 | 9/1978 | Bachur et al. | 315/151 |
| 4,643,571 | 2/1987 | Feber et al. | 356/326 |
| 5,029,245 | 7/1991 | Keranen et al. | 250/205 |
| 5,169,601 | 12/1992 | Ohta et al. | 422/73 |
| 5,281,540 | * 1/1994 | Merkh et al. | 436/530 |
| 5,491,329 | 2/1996 | Urakami et al. | 250/205 |

FOREIGN PATENT DOCUMENTS
0 115 294  8/1984  (EP).
0 286 142  12/1988 (EP).

OTHER PUBLICATIONS
*Research Disclosure*, Publication No. 40001, Aug. 1997, p. 483–484.

\* cited by examiner

*Primary Examiner*—Que T. Le

(57) ABSTRACT

A method of detecting an optical change in a series of test assays producing detectable results at varying efficiencies, the method comprising the steps of: a) selecting a test assay from the series, the selected assay having a known end-point photoresponse efficiency and a known filter center wavelength; b) providing a variable-intensity flash lamp illuminator comprising a lamp, a set of multiple filters with pre-selected center wavelengths assigned to particular assays, and a circuit for activating the lamp and comprising a capacitor, a power source, and a variable output voltage converter connected to the source and having its variable voltage output connected across the capacitor, the lamp and the filters providing a known level of system efficiency as a function of the center wavelength of the filter; c) providing a predetermined relationship of levels of illuminating intensities from the lamp as a function of photoresponse efficiencies of the assays and the system efficiencies, in which the photoresponse efficiencies of the assays are inversely proportional to the lamp intensities and the intensities are proportional to the square of the voltages applied to the lamp; d) selecting from the relationship a voltage applied to the lamp, and hence an intensity of the lamp, that corresponds to the known photoresponse efficiency of the assay selected in step (a) and its system efficiency based upon the filter center wavelength for the assay; and e) thereafter exposing the assay to the selected illuminating intensity.

10 Claims, 4 Drawing Sheets

METHOD OF PRESELECTING FLASHLAMP VOLTAGES FOR ASSAYS

This application claims benefit of provisional application 60/096,361 filed May 13, 1998.

FIELD OF THE INVENTION

This invention relates to a method for detecting optical changes in a test element using a lamp exposure, and the steps of selecting a voltage for the lamp to optimize the exposure level while extending the life of the lamp.

BACKGROUND OF THE INVENTION

It is known to provide feedback circuits in analyzers which alter in real time the output of illuminating devices, depending upon the level of signal detected at the detector. An example of such a system is shown in U.S. Pat. No. 5,491,329, which uses the irradiation on in vivo tissue samples. Such tissue samples of course are not known in advance as to their photoresponse efficiencies. Furthermore, the reason for the feedback circuit in such a system is to allow the proper use of the gain on the photomultiplier tube used in the detector. Such a use is irrelevant to detectors using flash lamps and simple photodiodes.

Yet another example of a real-time adjustment of the exposure device to reflect the system efficiencies of the optics is disclosed in U.S. Pat. No. 5,029,245. In this case, LEDs are modified during sample examination so that the radiation outputted is "regulated in accordance with the intensity data supplied [in real time] by the detector and in such manner that the radiation intensity of that wavelength range, and thus the intensity of the output radiation, is constant," column 4, lines 10–14.

Other examples of analyzers that adjust a lamp intensity depending upon the sample transmission detected in real time at a detector, but not preselected before exposure, are shown in, e.g., *Research Disclosure* Publication No. 40001, dated August 1997.

Although real-time adjustments are useful, they have the disadvantage of requiring fairly complex and sensitive optical systems, given the wide range of possible outputs and the lack of a priori control of outputs. Also, real-time adjustments necessitate some delay in the assay while changes are made in response to the reading, compared to the time needed for assays that have predetermined settings selected in advance. Furthermore, those that adjust simply on the basis of an instantaneous result do not provide any adjustment based on known performances of that particular assay as a whole.

Thus, there has been a need for a method of making energy level adjustments to illuminating devices in advance, for testing end-point assays selected from a list having known end-point photoresponse efficiencies, exposed in an optical system having a known system efficiency, without necessitating the complexities required for real-time adjustments.

As used herein, "photoresponse efficiencies" means, efficiencies dictated by the end-point photoresponsiveness of the chemistries used for a particular assay, and more specifically, the photoresponse that is determined from a plot of the photometric end-point density produced by the assay versus concentration of the analyte of that assay. In such plots, the steeper the curve, the more efficient is the photoresponse, and the less intense must be the illuminating device to obtain a satisfactory reading.

SUMMARY OF THE INVENTION

We have discovered a method of adjusting in advance the intensity of the illuminating device, based upon selecting an assay from a pre-selected list having known end-point photoresponse efficiencies and tested in an illuminating system having known system efficiencies that are a function of the center wavelength of exposure. The result is that the illumination intensity is optimal for that assay at that center wavelength, and specifically the power for that intensity is reduced for the more efficient assays and wavelengths, thus reducing the wear on and extending the life of, the illuminating device.

More specifically, there is provided a method of detecting an optical change in a series of test assays producing detectable results at varying efficiencies, the method comprising the steps of:

a) selecting a test assay from the series, the selected assay having a known end-point photoresponse efficiency and a known filter center wavelength;

b) providing a variable-intensity flash lamp illuminator comprising a lamp, a set of multiple filters with pre-selected center wavelengths assigned to particular assays, and a circuit for activating the lamp and comprising a capacitor, a power source, and a variable output voltage converter connected to said source and having its variable voltage output connected across the capacitor, the lamp and the filters providing a known level of system efficiency as a function of the center wavelength of the filter;

c) providing a predetermined relationship of levels of illuminating intensities from the lamp as a function of photoresponse efficiencies of the assays and the system efficiencies, in which the photoresponse efficiencies of the assays are inversely proportional to the lamp intensities and the intensities are proportional to the square of the voltages applied to the lamp;

d) selecting from the relationship a voltage applied to the lamp, and hence an intensity of the lamp, that corresponds to the known photoresponse efficiency of the assay selected in step (a) and its system efficiency based upon the filter center wavelength for the assay; and e) thereafter exposing the assay to the selected illuminating intensity, so that less intensity is used for assays having either higher photoresponse efficiencies or center wavelengths with a higher system efficiency, than is used for worst-case efficiency assays.

Because the photoresponse efficiencies are calculated in terms of densities, and not relative rates of change, the invention is particularly applicable to end-point assays.

Accordingly, it is an advantageous feature of the invention that voltage levels applied to a flashlamp illuminating device can be reduced in advance based upon known efficiencies of the assay to be illuminated, thereby extending the life of the flashlamp.

It is a related advantageous feature of the invention that the reduction in voltage levels can be based not only upon the known system efficiencies of the illuminating device, but also upon predetermined photoresponse efficiencies of the pre-selected assays.

Other advantageous features will become apparent upon reference to the following Detailed Description, when read in light of the attached drawings.

DESCRIPTION OF THE PREFERRED EMBODIMENTS

The invention is described in connection with certain preferred embodiments, wherein certain end-point assays with characteristic response efficiencies are selected for testing, the illuminating device is a flashlamp, the system efficiency is determined by a) the energy of the flash lamp at the center wavelength used for the assay in question, b) the filter providing that center wavelength, and c) the photodetector used, which is preferably a photodiode; and the circuit for activating the lamp comprises a single firing capacitor and a variable output voltage converter. In addition, the invention is applicable regardless of the end-point assays to be tested and their photoresponse efficiencies, regardless of the type of illuminating device, photodetector, or lamp-activating circuit that is used, and regardless of which components of the illuminator and detector contribute, and how much, to the system efficiency at certain center wavelengths of exposure.

Thus, the invention is preferably used with dried slide test elements premanufactured with the test reagents, currently available from Ortho-Clinical Diagnostics, Inc. under the trademark Vitros®, especially selected to assay for alcohol, glucose, conjugated and unconjugated bilirubin, total bilirubin, ammonia, albumin, protein, calcium, $CO_2$, magnesium, HDLC, cholesterol, lithium, phosphorus, lactate, blood urea nitrogen, salicilate, uric acid, triglycerides, amylase, and lipase, to name a few. Some of these are two-measurement end-point assays, at two different wavelengths.

Figure 1:
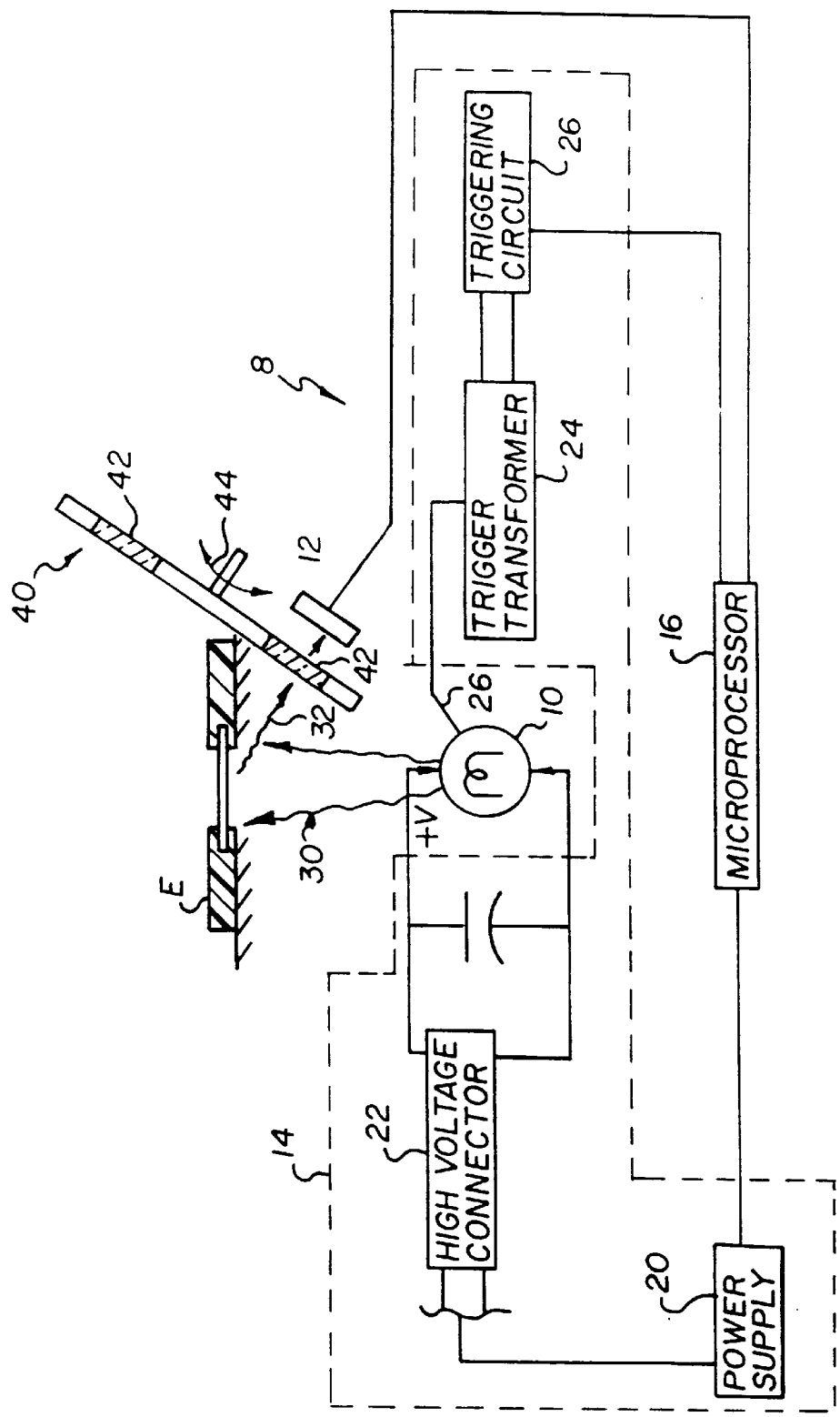
FIG. 1 is a schematic circuit diagram of a preferred reading station used in the method of the invention.

These are preferably assayed by being exposed to illumination delivered and detected on a clinical analyzer that is otherwise conventional, except for the following:

The read station 8 of that analyzer, FIG. 1, preferably comprises an illuminator flashlamp 10, a photodetector 12, an activating circuit 14 for firing the lamp 10, a microprocessor 16 for controlling circuit 14 and processing signals from detector 12, and a support 18 for a slide test element E of the type described above. Circuit 14 in turn preferably comprises a power supply 20, a variable output high voltage converter 22, a trigger transformer 24, a trigger pin 26, and a triggering circuit 26. All of the lamp 10, micro-processor 16, detector 12, power supply 20, voltage converter 22, trigger transformer 24, and triggering circuit 26 are conventional. For example, converter 22 can be a Model PS450 Flashtube Power Supply available from EG&G ElectroOptics, Inc.

FIG. 1 is particularly schematic in that rays 30 emanating from flashlamp 10 are shown as passing directly to element E, and reflected radiation 32 passing to detector 12 on a 90°–45° arrangement. In fact, this is only illustrative—the preferred mode of illumination is to first direct rays 30 into an integrating cavity that reflects diffuse radiation of no flash structure, onto element E. A representative useful example of such an integrating cavity with which flash lamp 10 can be associated is shown in the U.S. Pat. No. 4,660,984 (MacDonald). The details of that patent are expressly incorporated herein by reference.

Station 8 also preferably includes a filter wheel 40 with a plurality, and preferably eight of which only two are shown, filters 42. The wheel rotates, arrow 44, to position an appropriate filter in the path of the reflected radiation 32. (Auxiliary focusing lenses are not shown.)

Any filter wheel can be used. However, highly preferred is that described and claimed in commonly-owned U.S. application Ser. No. 08/873,155, filed on Jun. 11, 1997 entitled "Filter Wheel and Method Using Filters of Varying Thicknesses". Such wheel and method feature the following:

To eliminated the need for lenses altogether between wheel 40 and detector 12 filters 42 (and any others distributed about the circumference of the rotor 40 substantially equidistant from its axis) each have a significantly different thickness, that is, $t_1 \neq t_2 \neq t_i$ (for i filters). Additionally, the thicknesses are selected peculiar to the center wavelength of the bandpass for that filter, so that the focal distance is the same for all the filters, obviating the need for lenses between rotor 40 and detector 12.

The filters are most preferably eight (8) in number, selected to provide the assays of interest, a preferred selection of significantly different center wavelengths $\lambda_c$ for their bandpass, as noted in Table I below. In addition, each filter has the noted preferred maximum bandpass, although these values are not critical to the mathematical relationship set forth hereinafter, so long as the filters remain narrow bandpass filters.

TABLE I

| Filter Number | $\lambda_c$ ($\mu$m) | Maximum Bandpass (nm) |
|---|---|---|
| 1 | 0.340 | 26 |
| 2 | 0.400 | 12 |
| 3 | 0.460 | 22 |
| 4 | 0.540 | 11 |
| 5 | 0.600 | 12 |
| 6 | 0.630 | 13 |
| 7 | 0.670 | 9 |
| 8 | 0.680 | 13 |

Given these values for $\lambda_c$, the thicknesses for each filter are selected in accordance with the following predetermined formula:

$$t = \frac{S \cdot \sqrt{\frac{B_1 \lambda_c^2}{(\lambda_c^2 - C_1)} + \frac{B_2 \lambda_c^2}{(\lambda_c^2 - C_2)} + \frac{B_3 \lambda_c^2}{(\lambda_c^2 - C_3)} + 1}}{\left(\sqrt{\frac{B_1 \lambda_c^2}{(\lambda_c^2 - C_1)} + \frac{B_2 \lambda_c^2}{(\lambda_c^2 - C_2)} + \frac{B_3 \lambda_c^2}{(\lambda_c^2 - C_3)} + 1}\right) - 1}$$

wherein t=thickness of the filter in mm, S=change in focal length in mm due to the presence of the filter (a constant value, $\lambda_c$=the center wavelength in microns of the bandpass of the filter, and $B_1$, $B_2$, $B_3$, $C_1$, $C_2$, and $C_3$ are constants of the Sellmeier Dispersion Formula, available from glass manufacturers.

The above equation is derived from the Sellmeir Dispersion Formula, and Snell'Law simplified for use with small angles of incidence, namely S=(t/n) (n−1)wherein S+t are as defined above, and n is the index of refraction. Based on this equation, the filters have the preferred and unique thicknesses, for their given $\lambda_c$, set forth in Table II:

TABLE II

| Filter Number | Thickness (in mm) |
|---|---|
| 1 | 6.096 |
| 2 | 7.093 |
| 3 | 7.296 |
| 4 | 7.276 |
| 5 | 7.194 |
| 6 | 7.145 |
| 7 | 7.075 |
| 8 | 7.057 |

(The optical assembly of FIG. 1 with these filters is adjusted to provide an F number of 3.8.)

It will be appreciated that, for other values of $\lambda_c$ and "d", thicknesses different from those of Table I can be selected.

In use, wheel 40 is rotated so that only one or another of the plural filters therein (e.g., filter number 1, 2, ... 8) is selected at any one time to intercept the beam that is converging through the filter. The selection, of course, is made based upon the detectable wavelength that is optimized for a given test element E, as is well known.

It is not necessary that the detecting station use a filter wheel to move the various filters into position. Instead, a linearly-moveable frame can be used that is reciprocated back and forth, not shown.

THE INVENTION

Figure 2:
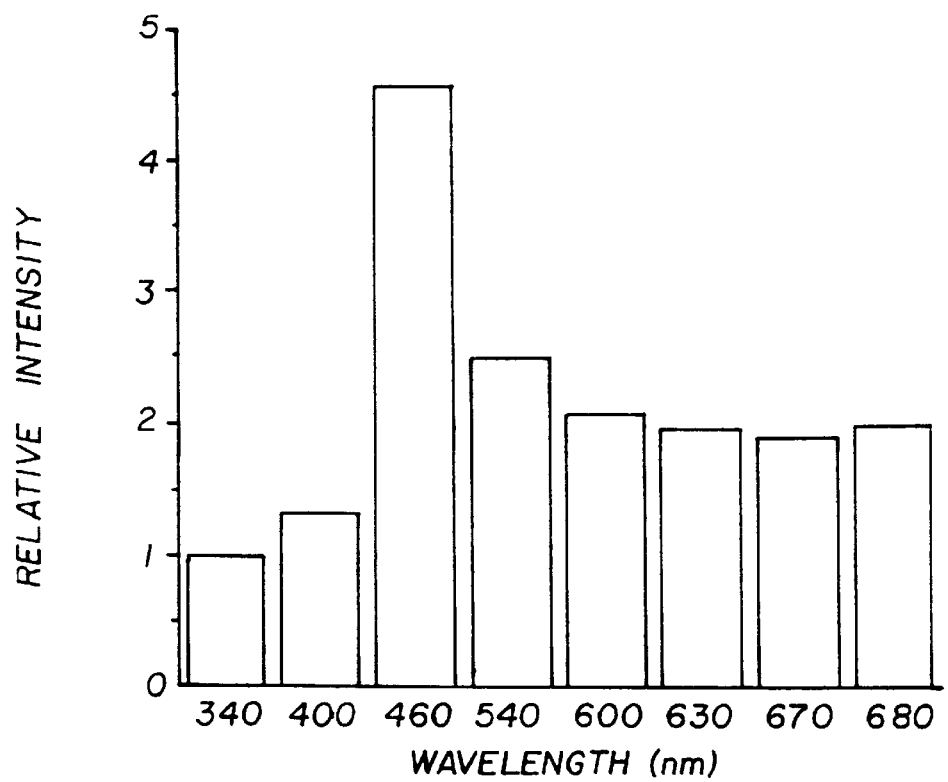
FIG. 2 is a plot of relative intensity of the illumination of the station shown in FIG. 1, as a function of the center-wavelength of the filter interposed in the path of the illuminating radiation, prior to the use of this invention.

As noted above, the optical system described for FIG. 1 has system efficiencies dictated by the flash energies of the lamp at the center wavelengths used for detection, the filters that provide such pass-through center wavelengths, and the photodetector. For a preferred optical system, the resulting relative intensities detectable at the various center wavelengths of interest (340, 400, 460, 540, 600, 630, 670, and 680) are shown in FIG. 2. That is, the system is most efficient at 460 nm, and least efficient at 340 nm (assigned an arbitrary value of 1.0). Furthermore, at 460 nm the system is about 4.6 times as efficient as it is at 340 nm, measured by relative intensities.

(It will be appreciated by those skilled in the art that these efficiencies and how they compare to each other will vary as the components of the optical system, and the choice of center wavelengths, vary. Whatever system is selected, the raw, relative intensities need only be measured at the center wavelengths of choice.)

Figure 3:
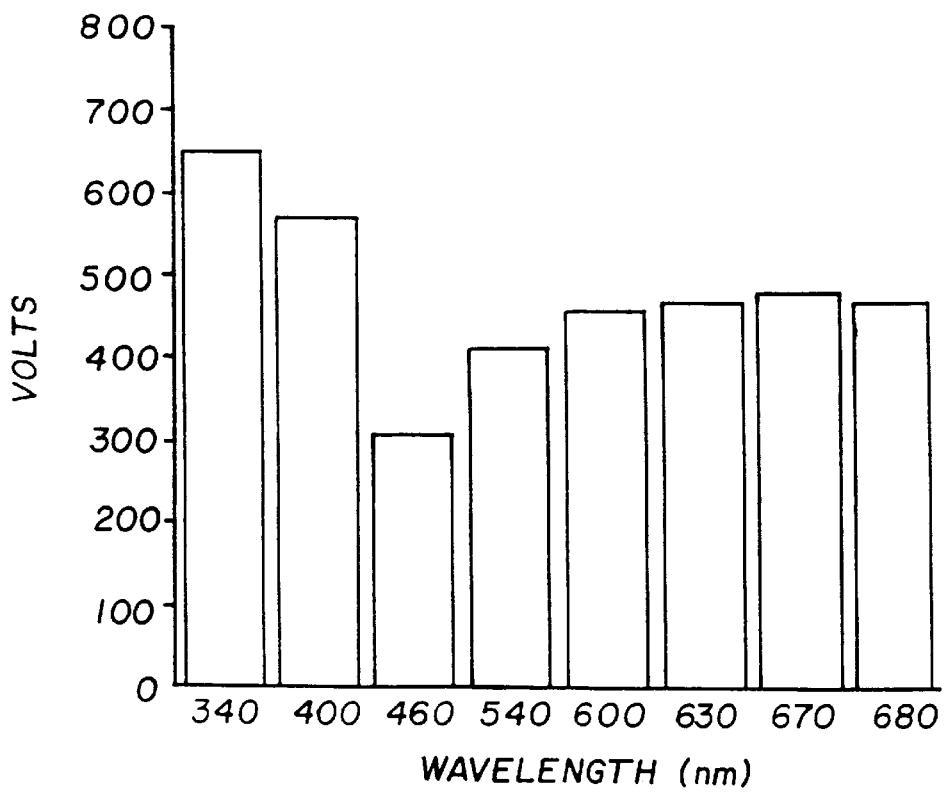
FIG. 3 is a plot of the voltage applied to the firing capacitor of the reading station of FIG. 1, when modified in accordance with one aspect of the invention.

Given the plot of FIG. 2, the next step is to assign the nominal full voltage value for the flashlamp to the weakest center wavelength—in this case, to the 340 nm center wavelength, FIG. 3. For a preferred flashlamp in question, the nominal full voltage value for a nominal full intensity exposure, is 650 volts. Because center wavelength 460 nm is about 4.6 times as efficient as 340 nm, the voltage to be applied to the flashlamp when using 460 nm center wavelength is determined as follows:

Flash energy E for the flashlamp is determined from the equation.

$E=\frac{1}{2}CV^2$, where C is the capacitance of the capacitor of FIG. 1 and V is the voltage $V^+$ applied to the flashlamp. Since a preferred capacitance value is 1 $\mu F$, then $E_{340}$ for the 650 volts applied at 340 nm (FIG. 2), becomes, $$E_{340}=\frac{1}{2}(1\times10^{-6})\,(650)^2=0.211 \text{ Joules}$$

It is already apparent from FIG. 2 that a 460 nm center wavelength measurement needs a flash energy that is 1/4.6 that of the 340 nm center wavelength. Or, the flash energy, $$E_{460}=E_{340}/4.6=0.211/4.6=0.046 \text{ Joules}.$$

However, $$E_{460}=\frac{1}{2}(1\times10^{-6})\,(V_{460})^2.$$

So solving for $V_{460}$, one finds that the voltage in FIG. 3 to be applied at 460 nm center wavelength is 305 volts.

In like manner, the voltages to be used for the other center wavelengths, adjusted to have a relative intensity equal to that of the 340 nm center wavelength, are determinable, and are the values shown in FIG. 3.

Thus, the voltages that are applied to the other center wavelengths fall in between 305 and 650.

Of the particular assays tested above, the center wavelengths listed in Table III are particularly useful:

TABLE III

| Wavelengths (nm) | | | | | | | |
|---|---|---|---|---|---|---|---|
| 340 | 400 | 460 | 540 | 600 | 630 | 670 | 680 |
| Alcohol | Conjugated and Unconjugated Bilirubin (2 measurements) | Glucose | Ammonia | | Albumin | Protein In Cerebral Spinal Fluid | Calcium |
| $CO_2$ | | Total Bilirubin (2 measurements) Cholesteral Lactate Salicylate Protein In Serum Triglyceride | Lithium | | Magnesium | HDLC Phosphorus Blood Urea Nitrogen Uric Acid | |

In this fashion, the voltage applied to the flashlamp is scaled down a priori from the nominal full value, for a given assay to be tested, depending on which center wavelength is used—unless, of course, the center wavelength is 340 nm. Hence, the lamp's lifetime is extended as it is not always flashed at its maximum intensity.

Still further, however, the fraction of the full nominal voltage to be used, whether equal to 1.0×650 volts in the case of the 340 nm , 305 volts in the case of 460 nm, or something in-between, is further modified depending on the endpoint photoresponse efficiency of the particular assay. This is determined, FIGS. 4 and 5, from the slope of a plot of the calibration curve of the particular assay, when compared to the extreme slope values illustrated here as being for triglyceride and for albumin. That is, the most efficient photoresponsiveness is shown in the slope of the triglyceride plot, and the least is shown in the slope of the albumin plot, where "slope" for purposes of this invention is measured as the change in the absolute value of the density units measured over the entire dynamic range of the assay.

Figure 4:
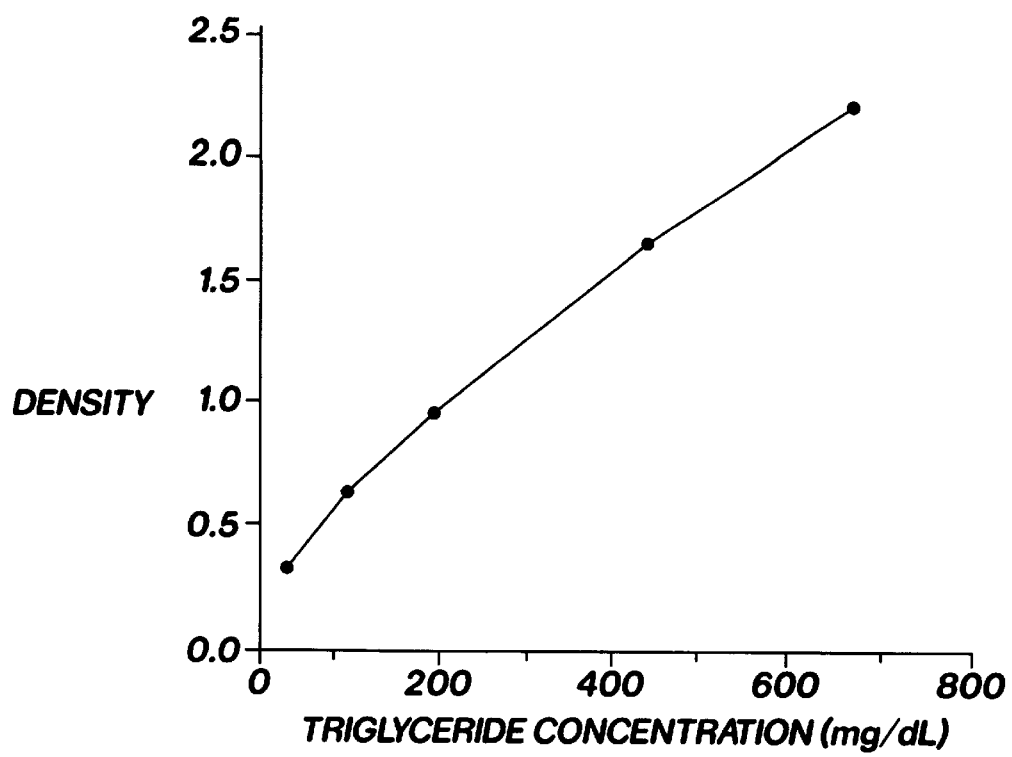
FIGS. 4 and 5 are plots of two different photoresponse curves, specifically of reflection density versus concentration on, FIG. 4 illustrating a maximum photoresponse efficiency example, and FIG. 5 illustrating a minimum photoresponse efficiency.
Figure 5:
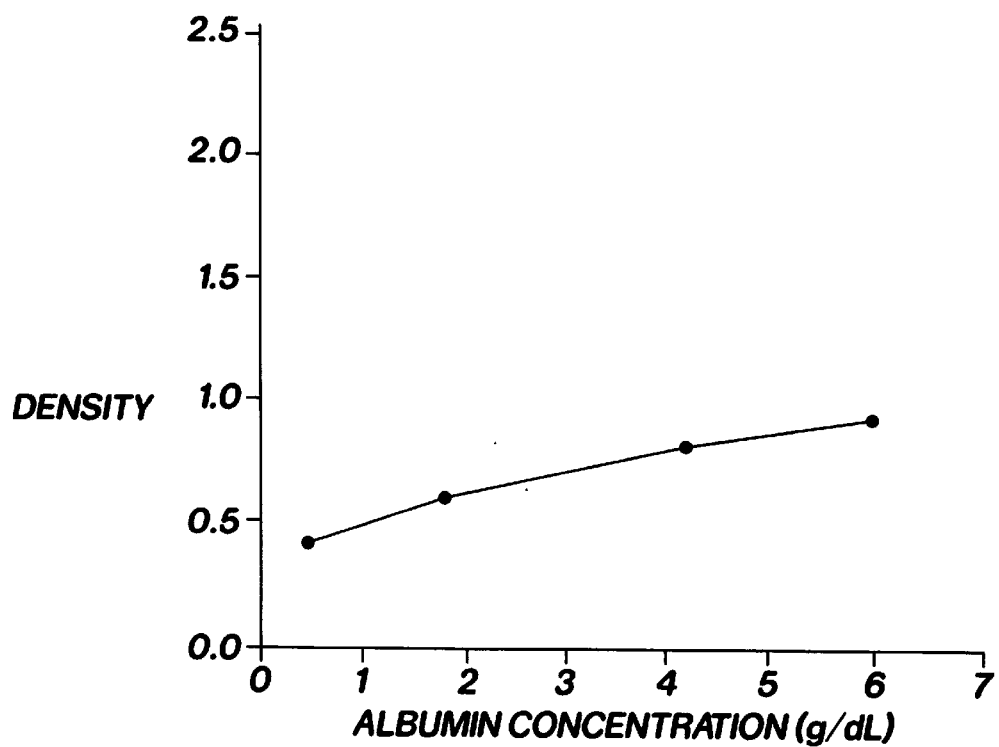

Thus, in FIG. 4, the dynamic range for triglyceride is from 10 to 525 mg/dL. ("Full dynamic ranges" as used in this application are those full ranges, based upon the analyzer and the reagent chemistries, that are published by an analyzer manufacturer as being reliable for use in a particular assay. It will be understood by those skilled in the art that these will vary from manufacturer to manufacturer, and over time.) As is seen from FIG. 4, the change in density units from 10 to 525 is from about 0.3 to about 1.8, or a slope of 1.5 density units over the dynamic range.

In contrast, the least efficient photoresponse curve of albumin produces a slope of (0.9–0.5), or 0.4 density units, measured over its dynamic range of from 1 to 6 g/dL.

Thus, a full value of lamp intensity is given to albumin's exposure, taking into account, however, that its reading at 630 nm has already reduced its voltage requirement, FIG. 3, to 475 volts instead of the full nominal value of 650 volts. That is, because albumin's photoresponse efficiency is the least efficient, its flashlamp voltage value of 475 volts is not further reduced.

However, all other assays are further reduced from the values shown in FIG. 3. More specifically, the exposure intensity shown in FIG. 3 is reduced by one-half if the slope of the calibration curve, over the full dynamic range, is as steep as that of FIG. 4, namely 1.5 density units. (This assumes that the assay in question has sufficient inherent precision such that a 50% reduction in illumination intensity will not render the assay so imprecise as to be outside acceptable clinical bounds.)

It is believed that all other assays listed in Table III have slopes between that of triglyceride and albumin, and are accordingly assigned a multiplier fraction in between ½ and 1. Thus, an assay whose slope is 0.95, or half-way between 0.4 and 1.5, is assigned a multiplier fraction of 0.75. Thus, if such an assay should use a center wavelength of 600 nm, the intensity to be applied to the flashlamp is only ¾ that used for 460 volts. Solving for $V_u$ in $(V_u)^2/(460)^2=0.75$, one gets a voltage of 398 for such a case. As one skilled will realize, in no case should the lamp voltage be reduced below the minimum operating voltage.

Figure 6:
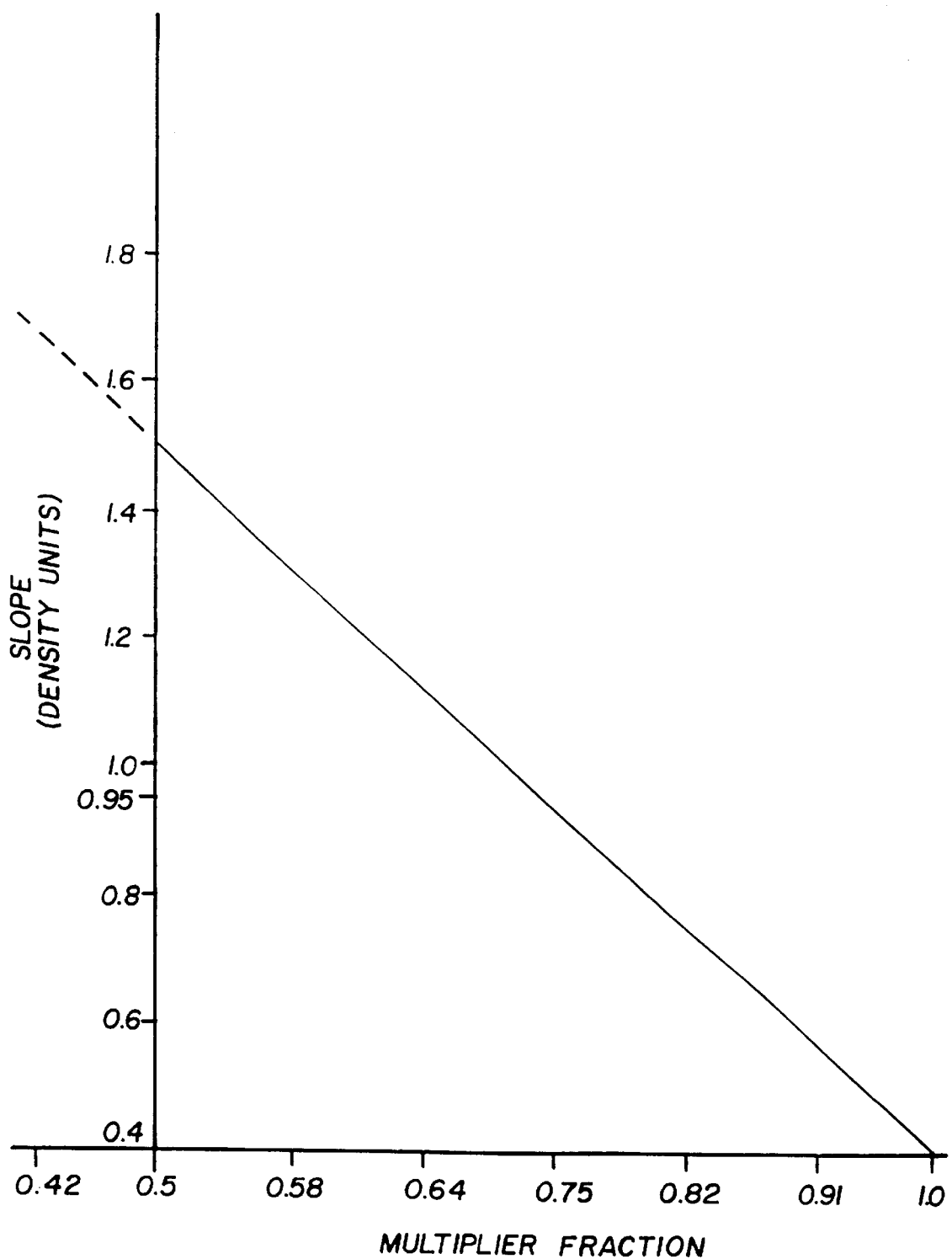
FIG. 6 is a plot of slopes obtained from the calibration curves of particular assays, against their photoresponse efficiency multiplier fractions, which vary from ½ to 1.

These values of multiplier fractions of 1.0 for 0.4 slope, 0.5 for 1.5 slope and ¾ for 0.95 slope, allow a transform plot to be drawn as in FIG. 6. Such a plot is used to determine the photoresponse efficiency multiplier fraction, based upon the slope of the calibration curve, for any assay.

Stated another way, the $CO_2$ assay is measured at 340 center wavelength, and has a photoresponse curve that produces a negative density change of 1.88 at 5 mmol/L, to 1.12 at 40 mmol/L, which is its full dynamic range. Or, the absolute value of the slope of $CO_2$ is 0.76 density units. From the plot of FIG. 6, one can determine that the multiplier to be used for the photoresponse efficiency of $CO_2$ is about 0.84. That is, since $CO_2$ is measured at the center wavelength of 340 nm, Table III, the nominal full value of 650 volts, FIG. 3, is multiplied by 0.84 to produce a voltage of about 545 volts, and 545 volts is the reduced flashlamp intensity that is used, preferably, to measure $CO_2$.

It is, of course, possible that an assay could produce a slope in its calibration curve that exceeds 1.5. In that case, whatever its value is as an extension of the plot of FIG. 6 into the next, upper left quadrant, shown as a dotted line, the appropriate multiplier fraction below 0.5 can be determined.

Likewise, should the slope of a calibration curve be less than .0.4, the plot of FIG. 6 can be extended, not shown, into the lower right quadrant to produce a multiplier fraction greater than 1.0. There is a limit, however, since much less than 0.4 produces a calibration curve having a too-low signal-to-noise ratio, as is well-known.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. A method of detecting an optical change in a series of test assays producing detectable results at varying efficiencies, the method comprising the steps of:

a) selecting a test assay from said series, said selected assay having a known end-point photoresponse efficiency and a known filter center wavelength;

b) providing a variable-intensity flash lamp illuminator comprising a lamp, a set of multiple filters with preselected center wavelengths assigned to particular assays, and a circuit for activating said lamp and comprising a capacitor, a power source, and a variable output voltage converter connected to said source and having its variable voltage output connected across said capacitor, said lamp and said filters providing a known level of system efficiency as a function of the center wavelength of the filter;

c) providing a predetermined relationship of levels of illuminating intensities from said lamp as a function of photoresponse efficiencies of said assays and said system efficiencies, in which the photoresponse efficiencies of said assays are inversely proportional to the lamp intensities and said intensities are proportional to the square of the voltages applied to said lamp;

d) selecting from said relationship a voltage applied to said lamp, and hence an intensity of the lamp, that corresponds to said known photoresponse efficiency of the assay selected in step (a) and its system efficiency based upon the filter center wavelength for said assay; and e) thereafter exposing said assay to said selected illuminating intensity, so that less intensity is used for assays having either higher photoresponse efficiencies or center wavelengths with a higher system efficiency, or both, than is used for worst-case efficiency assays.

2. A method as defined in claim 1, and further including the step of detecting light reflected from said assay using a photodiode.

3. A method as defined in claim 1, wherein said predetermined relationship comprises the step of assigning a nominal full level of illuminating intensity, $I_F$, and hence voltage applied to said lamp, to assays having a center wavelength of 340 nm, and reduced levels of illuminating intensities to assays having center wavelengths above said 340 nm.

4. A method as defined in claim 3, wherein said predetermined relationship is further defined by assigning said nominal full level of illuminating intensity, and hence applied voltage only to 340 nm wavelength assays having a density versus concentration photoresponse curve that is no steeper than a curve having a slope of an absolute value of 0.4 density units over the entire dynamic range of said assay.

5. A method as defined in claim 4, wherein said assigned level of illuminating intensity based upon the center wavelength is multiplied by a fraction less than 1.0 for a selected assay having a photoresponse curve whose slope is steeper than said slope of an absolute value of 0.4 density units over the entire dynamic range of said assay.

6. A method as defined in claim 5, wherein a selected assay having a photoresponse curve with a slope of an absolute value of 1.5 density units over the entire dynamic range of said assay, is exposed to said assigned level of illuminating intensity based upon center wavelength, multiplied by the fraction one-half.

7. A method as defined in claim 3, wherein for assays having a center wavelength of 460 nm, the predetermined relationship comprises the step of assigning the value of $0.5 \times I_F$ of illuminating intensity, and hence a value of $0.7 \times$ the applied voltage.

8. A method as defined in claim 7, and further including the steps of assigning a level of illuminating intensity to assays having center wavelengths that are other than 340 and 460 nm, that is between said nominal full level and said 0.7 of the full level of said voltage.

9. A method as defined in claim 8, wherein for said nominal full level of illuminating intensity, the voltage applied to said flashlamp is a voltage that is about 650 volts.

10. A method as defined in claim 1 wherein said step b) comprises providing a flashlamp as said illuminator and providing in said circuit, a firing capacitor and a variable output voltage converter having its variable voltage output connected across said capacitor, so that the voltage selected by said step d) is applied to the firing capacitor to fire the flashlamp at said selected intensity.

* * * * *